US00PP11635P

United States Patent [19]

Ogilvie

[11] Patent Number: Plant 11,635

[45] Date of Patent: Nov. 14, 2000

[54] SHRUB ROSE PLANT NAMED 'AC DE MONTARVILLE'

[75] Inventor: Ian S. Ogilvie, Pointe Claire, Canada

[73] Assignee: Her Majesty the Queen in right of Canada, as represented by the Minister of Agriculture, Ontario, Canada

[21] Appl. No.: 09/196,434

[22] Filed: Nov. 19, 1998

[51] Int. Cl.[7] ..... A01H 5/00

[52] U.S. Cl. ..... Plt./102

[58] Field of Search ..... Plt./102, 107, 108, Plt./141, 149, 150

[56] References Cited

PUBLICATIONS

Ogilvie, et al., 1999, "Three new winter–hardy Explorer rose cultivars", Hortscience 34(2):358–360. (Dialog(R)File 50:CAB Abstracts).

*Primary Examiner*—Howard J. Locker

*Attorney, Agent, or Firm*—Burns, Doane, Swecker & Mathis, L.L.P.

[57] ABSTRACT

A new and distinct variety of shrub rose plant is provided which forms at a low frequency per shoot attractive medium red blossoms that tend to fade to rose pink when fully mature. The new variety exhibits an upright growth habit with medium green foliage that exhibits medium glossiness on the upper surface, and good winter hardiness. The blossoms are star-shaped when viewed from above and are somewhat flattened with a convex lower portion when viewed from the side. Good resistance to powdery mildew and blackspot have been observed. The leaflets commonly number three or five per leaf. The new variety propagates well by the use of softwood stem cuttings, and is well adapted for growing as ornamentation in the landscape.

2 Drawing Sheets

SUMMARY OF THE INVENTION

The new *Rosa hybrida* variety of shrub rose plant of the present invention was created during 1982 by artificial pollination at the Central Experimental Farm, Ottawa, Ontario, Canada. The female parent (i.e., the seed parent) was an unnamed line designated 'A15' (non-patented in the United States) and the male parent (i.e., the pollen parent) was an unnamed line designated 'L76' (non-patented in the United States). Each parent had been previously studied in the hope that it would contribute the desired attractive characteristics to the product of the cross. 'A15' was a breeding line obtained in 1970 from a cross between the 'Queen Elizabeth' variety U.S. Plant Pat. No. 1,259) and the 'Arthur Bell' variety (non-patented in the United States). 'A76' was a breeding line obtained in 1972 from a cross between [*R. kordesii*×('Masquerade'×'Pink laxa') open-pollinated] and ['Red Pinocchio'×(Joanna Hill×*R. pimpinellifolia altaica*) open-pollinated]. Following observation of the offspring of this cross a single plant of the new variety was observed and selected.

The parentage of the new variety can be summarized as follows:

'A15'×'L76'.

It was found that the new variety of shrub rose plant of the present invention possesses the following combination of characteristics:

(a) exhibits a medium-sized upright growth habit with attractive medium green foliage that bears medium glossiness on the upper surface, (b) forms attractive double medium red blossoms that tend to fade to rose pink when fully mature, (c) propagates well by the use of softwood cuttings, (d) exhibits good winter hardiness, (e) exhibits good resistance to powdery mildew and blackspot, and (f) is particularly well suited for growing as ornamentation in the landscape.

The rose plants of the new variety can be grown well on their own roots out-of-doors without protection at L'Assomption, Quebec, Canada. The blossoms commonly appear continuously for approximately ten weeks beginning in late-June. Resistance to powdery mildew and blackspot has been observed to date.

When compared to 'Le Vésuve' variety (non-patented in the United States), the new variety of the present invention exhibits an upright growth habit unlike the bushy growth habit of the 'Le Vésuve' variety, forms blossoms that are medium red fading to rose pink as opposed to red-purple fading to purplish pink, and forms leaves of three or five leaflets per leaf as opposed to five leaflets per leaf.

The new variety well meets the needs of the horticultural industry. It can be grown to advantage as attractive ornamentation in parks, gardens, public areas, and residential landscapes.

The characteristics of the new variety have been found to be homogenous and stable and have been shown to be strictly transmissible by asexual propagation by the rooting of softwood stem cuttings conducted at Ottawa, Ontario, Canada, beginning in 1985.

The new variety has been named the 'AC De Montarville'. Also, the new variety is a member of the EXPLORER Series of hardy rose plants.

BRIEF DESCRIPTION OF THE PHOTOGRAPHS

The accompanying photographs show, as nearly true as it is reasonably possible to make the same in color illustrations of this character, typical three-year-old specimens of mature plants and plant parts of the new variety. The illustrated rose plants of the new variety were photographed during 1995 while growing on their own roots at L'Assomption, Quebec, Canada.

FIG. 1 — illustrates a typical specimen of a double medium red blossom during the course of opening. The glossy medium green foliage also is shown.

FIG. 2 — illustrates a typical flowering plant of the new variety while growing in the landscape. Fully mature blossoms which have faded to rose pink are illustrated.

DETAILED DESCRIPTION

Figure 1:
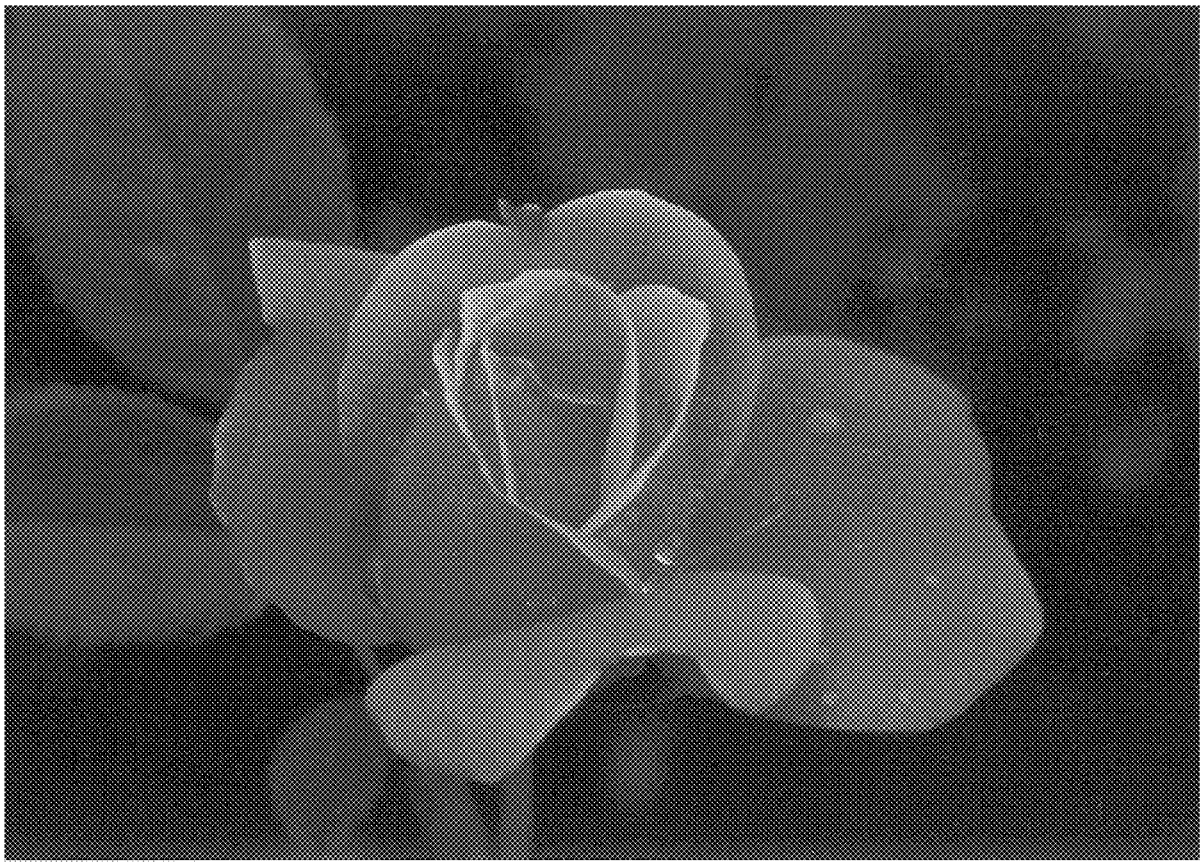
Figure 2:
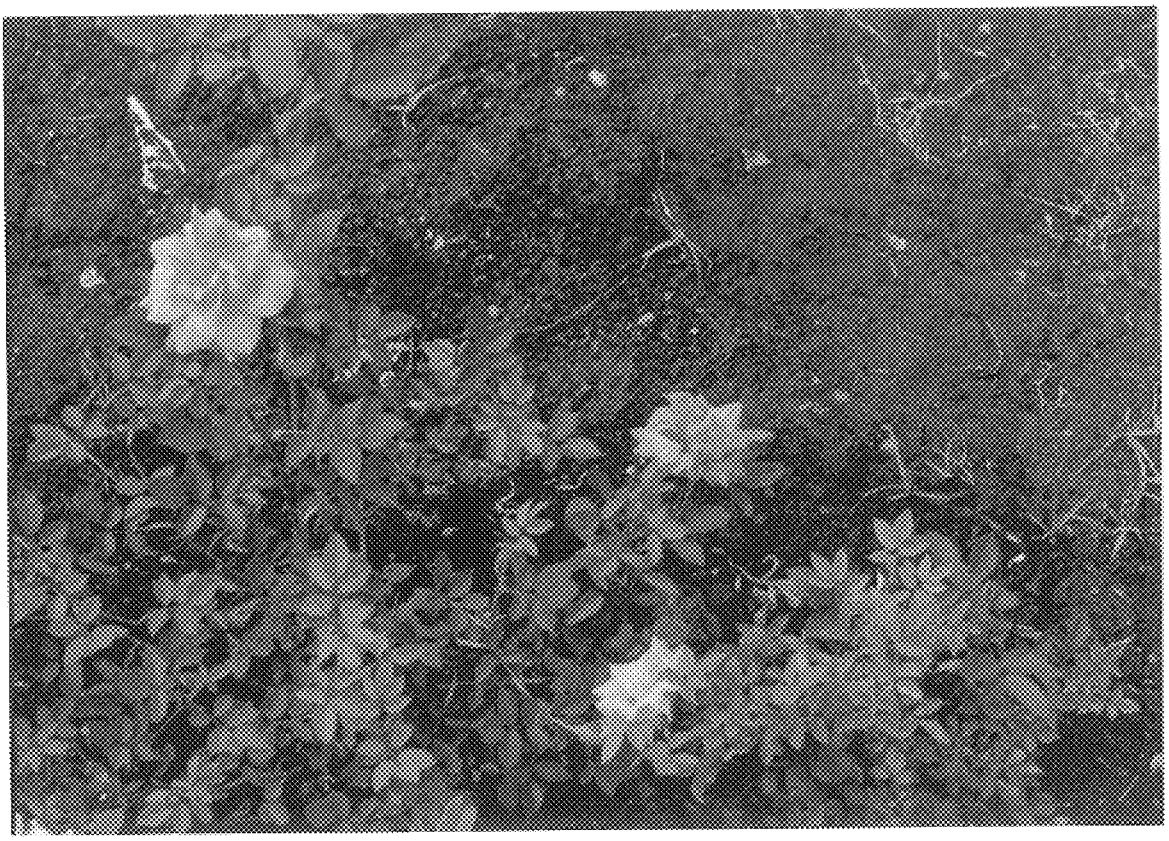

The chart used in the identification of colors is that of The Royal Horticultural Society (R.H.S. Colour Chart). Common color terms are to be accorded their ordinary dictionary significance. The description is based on the observation of mature plants of the new variety while being grown outdoors at L'Assomption, Quebec, Canada.

Class: Shrub.

Plant:

*Height.*—A mature plant commonly assumes a height of approximately 50 to 100 cm. and a width of approximately 100 cm. at the end of the growing season.

*Habit.*—Upright.

Thorns:

*Quantity.*—Short thorns (<5 mm.) are average in density and long thorns (>5 mm.) are sparse. Approximately 10 to 19 thorns commonly are displayed per 10 cm. of stem.

*Color.*—Greyed-Purple Group 185B.

*Configuration.*—Deep concave.

Leaves: Compound and pinnate.

*Leaflets.*—Number: 3 or 5. Shape: The terminal leaflet is smaller than that of the 'Le Vésuve' variety, is thin and has a rounded base (as illustrated). Margins: Serrate. Size: Commonly approximately 60 to 90 mm. (74.7 mm. mean) in length and approximately 35 to 60 mm. (48.5 mm. mean) in width on average. Texture: Thin. General appearance: Medium green with medium glossiness on the upper surface.

*Color.*—Adult foliage: Medium green, Yellow-Green Group 147A on the upper surface. Young foliage: Green Group 137D with some tones of Greyed-Purple Group 184B on the upper surface, and Green Group 138B with some tones of Greyed-Purple Group 187D on the under surface. Young shoots: Bear weak reddish-brown anthocyanin coloration.

*Petiole.*—Yellow-Green Group 146C with tones of Greyed-Purple Group 184B.

*Stipule.*—Yellow-Green Group 148B with tones of Greyed-Purple Group 185C.

Inflorescence:

*Number of flowers.*—Small number (e.g., commonly less than four) per shoot (as illustrated).

*Pedicel.*—Commonly bears a few thorns, and Yellow-Green Group 146D in coloration.

*Sepals.*—Absent or weak extensions, and commonly approximately 16 to 20 mm. (18.4 mm. mean) in length. Yellow-Green Group 146D with tones of Red-Purple Group 63B on the upper surface, and Yellow-Green Group 146D on the under surface.

*Buds.*—Shape: Globular in longitudinal section. Color upon opening: Red-Purple Group 63A when one-quarter open, and Red-Purple Group 58A on the upper surface and Red Group 52A on the under surface.

*Flower.*—Shape: Double with a normal center, star-shaped when viewed from above and tends to flatten with a flattened convex lower portion at full maturity as viewed from the side. Diameter: Commonly approximately 70 to 85 mm. (78.5 mm. mean). Diameters of 68 to 72 mm. have also been observed under different growing conditions. Color (when blooming): The overall blossom coloration initially is Red-Purple Group 67C, then changing to Red Group 55A, and when open the upper petal surface is Red Group 55B and under petal surface also is Red Group 55B. The coloration of the blossoms commonly fades to rose pink, near Red Group 55C (as illustrated) when the blossoms are fully mature. The petals have a medium-sized yellow spot at the base that is Yellow Group 7B and on the upper surface and also Yellow Group 7B on the under surface.

*Petal configuration.*—Possess weak reflexing and undulation.

*Fragrance.*—Weak.

*Petal number.*—Approximately 23 to 29 on average.

*Filaments.*—Yellow in coloration.

*Pollen.*—Yellow, Yellow Group 13B, and commonly sparsely formed.

*Style.*—Short, and yellow in coloration with weak pubescence on the upper one half.

*Stigma.*—Commonly disposed at the same level as the anthers.

*Petal drop.*—Petals commonly detach cleanly to produce a good petal drop.

*Receptacle.*—Small and in the shape of a pitcher, and commonly without prickles.

*Lasting quality.*—A blossom commonly lasts approximately 5 to 7 days on the plant depending upon environmental conditions (primarily temperature) encountered.

*Duration.*—Blossoms commonly are formed beginning in mid-season (e.g., approximately June 24 th) continuously over a period of 10 weeks or more when grown in the landscape.

*Hips.*—None observed to date.

Development:

*Blossoming.*—Continuous.

*Hardiness.*—Has survived winter temperatures of −28° C. to −35° C.

*Resistance to diseases.*—Is resistant to powdery mildew [*Sphaerotheca pannosa* (Wallr. ex Fr.) Lev.] and blackspot (*Diplocarpon rosae* Wolf.) during observations to date.

*Preferred mode of propagation.*—The use of softwood cuttings to produce self-rooted plants is recommended. For instance, softwood cuttings taken at the bud stage can be dipped in rooting powder (e.g., Stimroot No. 2, 0.4 percent indolebutyric acid of Plant Products, Bramalea, Ontario, Canada) and placed under mist for 3 to 4 weeks at 20 to 25° C. ambient temperature. Tissue culture and grafting also can be utilized. However, the latter is not recommended for optimum hardiness.

I claim:

1. A new and distinct variety of shrub rose plant characterized by the following combination of characteristics:

(a) exhibits a medium-sized growth habit with attractive medium green foliage that bears medium glossiness on the upper surface, (b) forms attractive double medium red blossoms that tend to fade to rose pink when fully mature, (c) propagates well by the use of softwood cuttings, (d) exhibits good winter hardiness, (e) exhibits good resistance to powdery mildew and blackspot, and (f) is particularly well suited for growing as ornamentation in the landscape;

substantially as herein shown and described.

* * * * *